(12) United States Patent
Dardona et al.

(10) Patent No.: US 8,785,874 B2
(45) Date of Patent: Jul. 22, 2014

(54) IONIZATION WINDOW

(75) Inventors: Sameh Dardona, South Windsor, CT (US); Timothy N. Obee, South Windsor, CT (US); Marcin Piech, East Hampton, CT (US); Joseph V. Mantese, Ellington, CT (US)

(73) Assignee: Walter Kidde Portable Equipment, Inc., Mebane, NC (US)

( * ) Notice: Subject to any disclaimer, the term of this patent is extended or adjusted under 35 U.S.C. 154(b) by 0 days.

(21) Appl. No.: 13/976,657

(22) PCT Filed: Dec. 30, 2010

(86) PCT No.: PCT/US2010/062495
§ 371 (c)(1),
(2), (4) Date: Jun. 27, 2013

(87) PCT Pub. No.: WO2012/091715
PCT Pub. Date: Jul. 5, 2012

(65) Prior Publication Data
US 2013/0270446 A1     Oct. 17, 2013

(51) Int. Cl.
*G01T 1/185*     (2006.01)

(52) U.S. Cl.
USPC ..................................................... 250/382

(58) Field of Classification Search
USPC ..................................................... 250/382
See application file for complete search history.

(56) References Cited

U.S. PATENT DOCUMENTS

| 4,564,762 | A | * | 1/1986 | Doherty et al. ............... 250/381 |
| 4,712,008 | A | * | 12/1987 | Vora et al. ..................... 250/287 |
| 5,160,843 | A | | 11/1992 | Lehto |
| 5,345,083 | A | | 9/1994 | De Koning |
| 5,989,931 | A | | 11/1999 | Ghodsian et al. |
| 6,023,169 | A | | 2/2000 | Budovich et al. |
| 6,362,484 | B1 | | 3/2002 | Beyne et al. |
| 6,429,426 | B1 | | 8/2002 | Doring |
| 6,586,729 | B2 | | 7/2003 | Doring |
| 6,740,874 | B2 | | 5/2004 | Doring |
| 7,084,401 | B2 | | 8/2006 | Bell et al. |
| 7,483,139 | B2 | | 1/2009 | Powell |
| 7,576,331 | B2 | | 8/2009 | Allsworth et al. |
| 2009/0246084 | A1 | | 10/2009 | Wilbertz et al. |
| 2010/0006751 | A1 | | 1/2010 | Bather et al. |
| 2010/0032560 | A1 | | 2/2010 | Allsworth |
| 2010/0066380 | A1 | | 3/2010 | Knapp et al. |

OTHER PUBLICATIONS

International Search Report and Written Opinion for International application No. PCT/US2010/062495 dated Sep. 1, 2011.

* cited by examiner

*Primary Examiner* — Kiho Kim
(74) *Attorney, Agent, or Firm* — Carlson, Gaskey & Olds

(57) ABSTRACT

An exemplary ionization window assembly includes a support layer having a thickness between a first side and a second side. There is at least one opening in the support layer extending between the first and second sides. The opening has a first width dimension near the first side of the support layer and a second, larger width dimension near the second side of the support layer. A window layer is supported on the second side of the support layer. The window layer extends across the opening to allow ionizing radiation to pass through the opening in a direction from the first side toward the second side.

27 Claims, 2 Drawing Sheets

IONIZATION WINDOW

BACKGROUND

There are a variety of detectors that rely upon ionization. For example, ionization is used to ionize gas molecules for detecting the presence of a particular gas or substance.

There are well known ionization sources including Ni63 and Americium 241. Both of these are radioactive. Ni63 is used in ion mobility spectrometry (IMS) and field asymmetric ion mobility (FAIMS) detectors and other applications where high energy, high flux ionization is required. FAIMS, for example, is highly sensitive and selective for toxic and combustible gas detection. Americium 241 is used in smoke detectors, for example.

The ionization in a detector will ionize air or another gas within a test chamber. The test chamber typically has a metal plate that is maintained at a positive voltage. Molecules within the chamber that have been ionized are accelerated toward the plate. A portion of the ions collide with a collector electrode located between the ionization source and the plate. Ions that collide with the plate generate a current and ions that collide with the collector electrode also generate a current. The ratio of these currents is compared to determine whether a substance of interest is present.

One drawback associated with known detectors is that they include a radioactive material within the ionization source. Another drawback is that the source of radioactive particles does not provide a consistent or tunable energy level.

One suggestion for avoiding radioactive materials within an ionization source is to use soft x-rays for ionization. One such example arrangement is shown in the United States Patent Application Publication No. U.S. 2010/0032560.

One challenge associated with using an x-ray or electron source for ionization is that it requires a vacuum within an enclosed chamber to sufficiently accelerate the electrons from an electron emission source. Given that many ionization devices utilize very small components, it is difficult to establish a window that allows electrons or x-rays to pass and that is mechanically strong enough to withstand the pressure differential across the window.

SUMMARY

An exemplary ionization window assembly includes a support layer having a thickness between a first side and a second side. There is at least one opening in the support layer extending between the first and second sides. The opening has a first width dimension near the first side of the support layer and a second, larger width dimension near the second side of the support layer. A window layer is supported on the second side of the support layer. The window layer extends across the opening to allow ionizing radiation to pass through the opening in a direction from the first side toward the second side.

An exemplary detector includes a pressurized chamber. A source of ionizing radiation (e.g., a source of x-rays or electrons) is situated at least partially in the chamber. An ionization window on at least one side of the chamber allows the ionizing radiation to exit the chamber. The ionization window includes a support layer having a thickness between a first side and a second side. There is at least one opening in the support layer extending between the first and second sides. The opening is wider near the second side than it is closer to the second side and the chamber. In other words, the opening has a first width dimension near the first side of the support layer and a second, larger width dimension near the second side of the support layer. A window layer is supported on the second side of the support layer. The window layer extends across the opening to allow ionizing radiation to pass through the opening in a direction from the first side toward the second side and to exit the chamber. A sensor near the ionization window senses whether molecules outside the chamber are ionized.

An exemplary method of making an ionization window includes establishing a plurality of support members on a wafer. The support members are arranged in a grid having a plurality of spaces between the support members. A first width dimension is established near one end of each of the spaces. A second, larger width dimension is established near a second end of each of the spaces. The support members and the wafer in the spaces are coated with a continuous ionization window layer. Material of the wafer adjacent the ionization window layer is removed at the spaces between the support members to leave only the ionization window layer across the openings near the one end of the spaces.

The various features and advantages of a disclosed example will become apparent to those skilled in the art from the following detailed description. The drawings that accompany the detailed description can be briefly described as follows.

DETAILED DESCRIPTION

Figure 1:
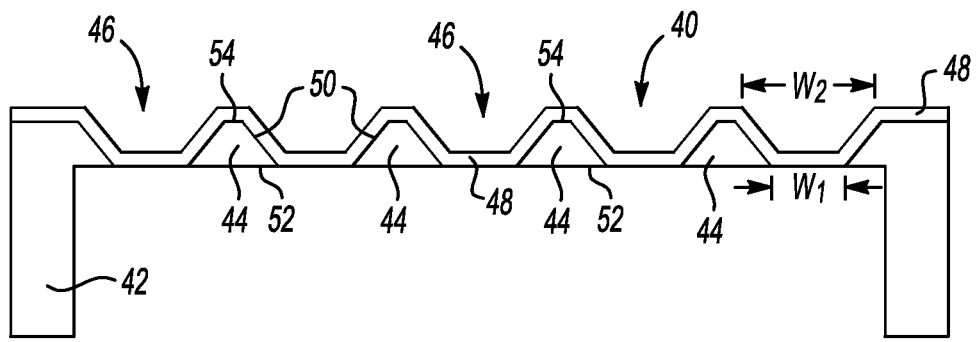
FIG. 1 schematically illustrates an ionization window assembly designed according to an embodiment of this invention.

FIG. 1 schematically shows an example configuration of an ionization window 40. A wafer 42 provides a base of material for establishing a support layer comprising a plurality of support members 44 in a grid pattern. In one example, the grid pattern of the support members 44 comprises a honeycomb-shaped pattern. Another example includes another geometric pattern. The support members 44 in FIG. 1 are shown in cross-section.

The grid pattern of the support members 44 includes a plurality of openings or spaces 46 between the support members 44. A window layer 48 is supported on the support members 44 and extends across the openings or spaces 46. The window layer 48 extending across the spaces or openings 46 provides passage for ionizing radiation such as electrons or x-rays to pass through the window 40 so that they are useful for a desired purpose such as ionizing a gas within a detector device.

The illustrated example has an ionization window 40 that is structurally sound enough to withstand the pressure required for using ionizing radiation comprising electrons or x-rays, for example. The example ionization window can be made small enough to fit within the miniaturized design required to fit within the packaging envelope of a variety of devices and allows for efficient ionizing radiation transmission. Each of the support members 44 has a first side 52 facing toward the source of the ionizing radiation (e.g., an electron or x-ray source). An opposite, second side 54 of the support members 44 faces outward toward the direction along which the ionizing radiation will move away from the window 40.

As can be appreciated from FIG. 1, the example support members 44 have a trapezoid-shaped cross-section. In some examples, the same cross-section exists in a perpendicular direction to that shown in FIG. 1. The actual shape of a particular embodiment of the support members 44 will depend on the processing conditions used to fabricate the structure. Each support member 44 has a sloped side surface 50 defining one side of an adjacent opening 46. The amount of material at the first sides 52 is greater than the amount of material at the second sides 54. This configuration establishes a first width dimension W1 on one side of the openings or spaces 46 and a second, larger width dimension W2 on an opposite side of the openings or spaces 46. The width dimension W2 is the largest dimension of the openings 46. The width dimension in this example progressively increases from W1 to W2. The increasing width dimension of the openings 46 in the direction of travel of the ionizing radiation facilitates better electron or x-ray emission through the ionization window 40. The widening openings in the direction of travel of the ionizing radiation (e.g., from the first side 52 toward the second side 54 of the support members 44) decreases the likelihood for electron or x-ray collision to interfere with efficient electron emission into a detection chamber, for example.

The openings 46 in most examples have a larger cross-sectional area on the side that includes the larger width W2 compared to the cross-sectional area on the side that includes the smaller width W1. In some examples, the width dimension increases in two perpendicular directions. In some such examples, the width dimension in each direction increases an equal amount so that the cross-section has consistent proportions along the entire depth or thickness of the openings.

The trapezoid-shaped cross-section of the support members 44 in this example has an isosceles trapezoid shape. The trapezoid cross-section provides increased structural strength because of the larger amount of material at the first sides 52 of the support members 44.

The trapezoid cross-section also facilitates a stronger ionization window 40 because the window coating layer 48 can more consistently coat all of the second sides 54 and the side surfaces 50 of the support members 44 and extend across each of the openings 46. Having a more consistent thickness of the window layer 48 across the entire window 40 improves the strength of the coating and establishes a better vacuum seal.

The trapezoid cross-section of the support members 44 allows for more consistent conformity of the window layer 48 with the geometry or configuration of the support members 44. Each of the angles or transition points along the support members at which the window layer 48 is applied includes an oblique angle between adjacent surfaces. By having oblique angles (all greater than 90° in this example) between adjacent surfaces on the support members 44 and between a plane of the openings 46 and adjacent support member side surfaces 50 allows for achieving a more consistent conformity of the window layer 48 to the support members 44 and a more consistent thickness of the window layer 48. Each of those features enhances the structural integrity of the window 40.

The window layer 48 is not as thick as the support members 44 in the direction of travel of the ionizing radiation (e.g., from the first side 52 toward the second side 54 of the support members 44). The support members 44 of the support layer have a first thickness in the direction from the first side 52 toward the second side 54 and the window layer 48 has a second, smaller thickness in that direction.

Figure 2:
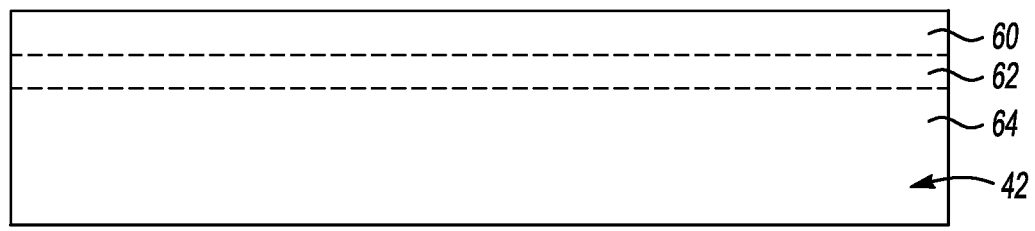
FIG. 2 schematically shows a wafer during an initial stage of making an ionization window like the example of FIG. 1.

One example method of making the ionization window 40 includes starting with a wafer as schematically shown in FIG. 2. In this example, the wafer 42 comprises silicon. This particular example includes a silicon layer 60, an insulator layer 62 and a silicon layer 64. This is a known three-layer wafer having a 10 micrometer layer of silicon 60, a 1 micrometer oxide layer 62 and a 300 micrometer silicon layer 64. The wafer 42 provides the material for establishing the support members 44. In this example, one side (the upper side according to the drawing) is etched using a pattern to establish the support members in a desired grid pattern using a known etching technique such as TMAH or anisotropic etching.

Figure 3:
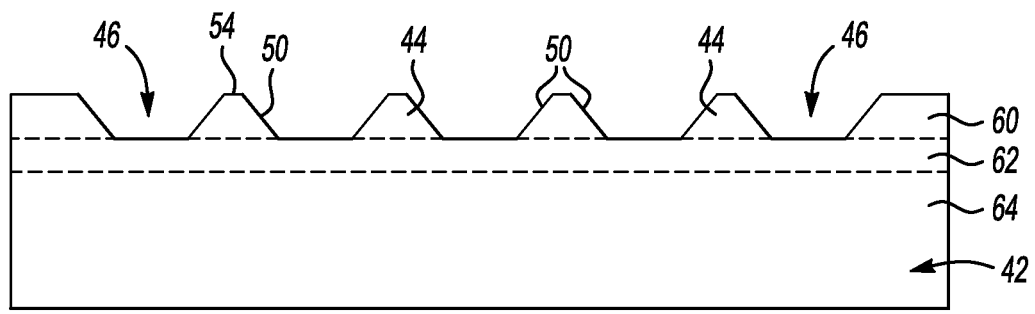
FIG. 3 schematically illustrates the wafer of FIG. 2 in a condition during a later stage of the example process of making the ionization window.

An example result of an etching procedure is schematically shown in FIG. 3. A $SiO_2$ layer 62 is effective as an etch stop for the etching technique used to establish the support members. In this example, one side of the silicon oxide wafer now includes the established sloped side surfaces 50 and the sides 54 of the support members 44.

Figure 4:
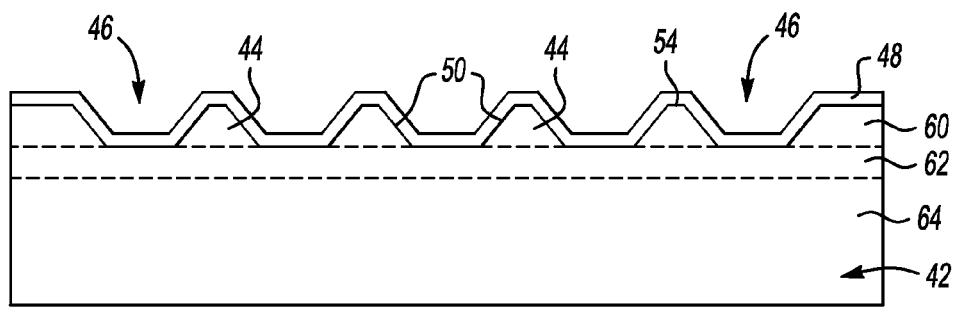
FIG. 4 schematically illustrates the wafer of FIGS. 2 and 3 during a subsequent stage of the example process of making the ionization window when a window layer has been applied to the wafer.

Using the configuration of FIG. 3, a coating of the window layer 48 is applied to coat the sides 54 and the sloped side surfaces 50 of the support members 44. The coating of the window layer 48 is also applied to the wafer material that is exposed across the spaces 46 between the partially formed support members 44. An example result of the coating process is schematically shown in FIG. 4.

Example materials for the window layer 48 comprise beryllium, carbon, graphite, boron nitride, aluminum, titanium, silicon nitride, silicon dioxide, aluminum oxide, magnesium oxide, silicon carbide, silicon oxynitride, silicon carbonitride, beryllium oxide, an ultra-nonocrystalline diamond or a combination of dielectric materials having low atomic weight. Given this description, those skilled in the art will realize which of those materials will best meet the needs of their particular situation. The selected material or combination of such materials should provide for consistent conformity between the window layer 48 and the support members 44, consistent thickness of the window layer 48 across the window 40, high transmission of the ionizing radiation (e.g., electrons or x-rays) and sufficient strength to withstand the high pressure differential across the window 40.

Figure 5:
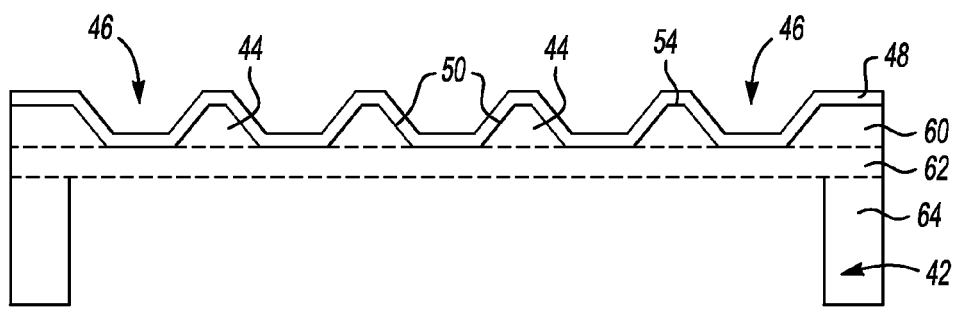
FIG. 5 schematically illustrates the wafer of FIG. 4 during a subsequent stage of the example process.

Once the window layer 48 has been established, a portion of the wafer 42 can be removed to expose the window layer 48 at the spaces or openings 46 to establish the portions of the ionization window 40 through which electrons may be transmitted. One example includes using a deep reactive ion etching technique for removing a portion of the silicon wafer 42. In this example, some of the layer 64 is removed so that the configuration schematically shown in FIG. 5 is the result of etching the configuration schematically shown in FIG. 4. As schematically shown in FIG. 5, the SiO2 layer 62 is exposed and still adjacent the window layer 48. One example includes using a buffered hydrofluoric acid etching technique for removing the layer 62. The resulting ionization window 40 shown in FIG. 1 is structurally sound enough to withstand the high pressure differential across the window 40 that will be required in many devices that incorporate such an ionization window. At the same time the window 40 can be made small enough to be incorporated into a miniaturized device configuration and provides for efficient transmission of the ionizing radiation.

Figure 6:
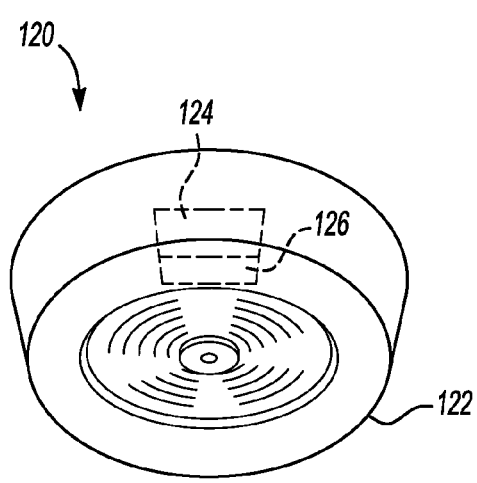
FIG. 6 schematically shows an example detector including an ionization window designed according to an embodiment of this invention.

There are a variety of devices into which an ionization window 40 may be incorporated. FIG. 6 illustrates one example detector device 120. This example is a smoke detector for discussion purposes only as the disclosed example ionization window is not necessarily limited to a specific detector. Smoke will be used as an example substance or fluid of interest. Other gases may be detected in some examples.

A housing 122 supports several components that are useful for detecting smoke in an area of interest in a generally known manner. Of those components, an ionization source 124 and a detection area 126 are schematically illustrated in phantom in FIG. 6. The ionization source 124 in this example uses electrons or x-rays for ionizing air within the detection area 126. When smoke enters the detection area 126, the number of free ionized air molecules decreases as some of them bind to the smoke particles. This results in a decreased ionization current and that provides an indication that the smoke detector device 120 should provide or initiate an alarm.

Figure 7:
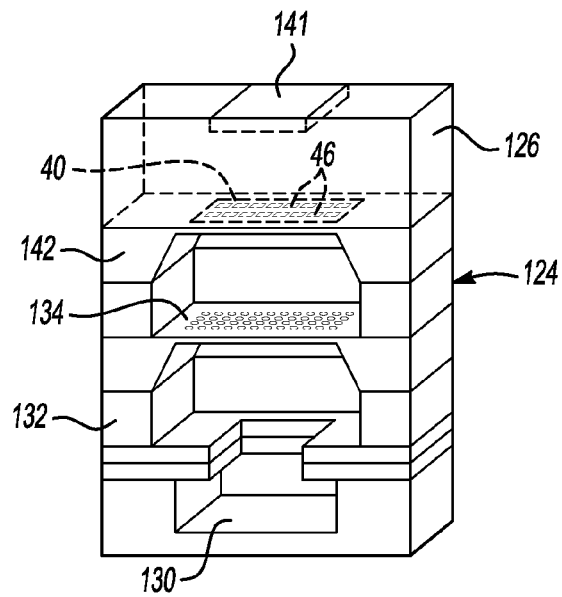
FIG. 7 schematically illustrates selected components of an example detector device.

FIG. 7 schematically shows one example ionization device 124 and an associated detection area 126. In this example, a source 130 of ionizing radiation is a miniaturized x-ray or electron source. One example includes a cold cathode emitter such as carbon nanotubes. Another example includes using ZnO field or thermal nanoneedle emitters. The ionizing radiation source 130 produces ionizing radiation (e.g., electrons or x-rays) for ionizing molecules in the detection area 126.

The ionizing radiation originating from the source 130 passes through a pressurized chamber 132 and travels toward the detection area 126. The chamber 132 is maintained at a low pressure or vacuum pressure. This example includes an accelerating grid 134 for directing the ionizing radiation toward an ionization window 40 at one end of the vacuum chamber 132. The ionizing radiation passes through the ionization window 40 and ionizes gas within the detection area 126. The illustrated example includes a sensor 141 that provides an indication of a detected amount of ionized air (or other fluid) within the detection area 126. Sensor 141 works in a known manner in one example.

The chamber 132 in one example includes a low pressure region on the order of one microtorr. The pressure differential across the window requires structural integrity of the ionization window 40 and the supporting structure to prevent the window 40 from being damaged and for maintaining the desired pressure within the chamber 132. The detection area 126 on the other side of the ionization window 40 is typically at ambient pressure.

The preceding description is exemplary rather than limiting in nature. Variations and modifications to the disclosed examples may become apparent to those skilled in the art that do not necessarily depart from the essence of this invention. The scope of legal protection given to this invention can only be determined by studying the following claims.

We claim:

1. An ionization window assembly, comprising:
a support layer having a thickness between a first side and a second side, at least one opening in the support layer extending between the first and second sides, the at least one opening having a first width dimension near the first side of the support layer and a second, larger width dimension near the second side of the support layer; and
a window layer supported on the second side of the support layer, the window layer extending across the at least one opening to allow ionizing radiation to pass through the at least one opening in a direction from the first side toward the second side.

2. The assembly of claim 1, wherein the window layer comprises at least one of a silicon oxide, a silicon nitride or a silicon oxynitride.

3. The assembly of claim 1, wherein the window layer comprises ultra-nanocrystalline diamond.

4. The assembly of claim 1, wherein the support layer comprises silicon.

5. The assembly of claim 4, wherein the support layer comprises a silicon-on-insulator wafer having silicon on opposite sides of an oxide.

6. The assembly of claim 1, wherein the support layer has a first thickness in the direction from the first side toward the second side and the window layer has a second, smaller thickness in the direction from the first side toward the second side.

7. The assembly of claim 1, wherein the at least one opening has a progressively increasing width from the first side to the second side and wherein the second width is the largest width of the opening.

8. The assembly of claim 1, wherein the support layer comprises a plurality of support members and a plurality of openings between support members, each support member having side surfaces facing toward an adjacent one of the openings, the side surfaces being aligned at an oblique angle relative to the first side of the support layer.

9. The assembly of claim 8, wherein at least some of the support members have a cross-section that is shaped as an isosceles trapezoid.

10. The assembly of claim 8, wherein the window layer comprises a continuous coating over the first side of the support members, the side surfaces of the support members and across the openings.

11. The assembly of claim 1, wherein the at least one opening has a first cross-sectional area near the first side and a second, larger cross-sectional area near the second side.

12. The assembly of claim 1, wherein the window layer maintains a desired pressure difference between a pressure on a first surface of the window layer near the first side and a second surface of the window layer that is closer to the second side than the first surface.

13. The assembly of claim 1, wherein the window layer has a first surface aligned with the first side of the support layer.

14. The assembly of claim 1, wherein the window layer comprises at least one of silicon dioxide, carbon, nitride, aluminum, titanium, beryllium, aluminum oxide, magnesium oxide, silicon carbide, silicon carbonitride, or beryllium oxide.

15. A detector, comprising:
a pressurized chamber;
a source of ionizing radiation at least partially in the chamber;
an ionization window on at least one side of the chamber that allows the ionizing radiation to exit the chamber, the ionization window including
a support layer having a thickness between a first side and a second side, at least one opening in the support layer extending between the first and second sides, the at least one opening having a first width dimension near the first side of the support layer and a second, larger width dimension near the second side of the support layer; and
a window layer supported on the second side of the support layer, the window layer extending across the at least one opening to allow the ionizing radiation to pass through the at least one opening in a direction from the first side toward the second side and to exit the chamber.

16. The detector of claim 15, wherein the window layer comprises at least one of a silicon oxide, a silicon nitride, a silicon oxynitride or ultra-nanocrystalline diamond.

17. The detector of claim 15, wherein the support layer comprises a silicon-on-insulator wafer having silicon on opposite sides of an oxide.

18. The detector of claim 15, wherein the support layer has a first thickness in a direction that the electrons exit the chamber and the window layer has a second, smaller thickness in the direction.

19. The detector of claim 15, wherein the at least one opening has a progressively increasing width from the first side to the second side and wherein the second width is the largest width dimension of the opening.

20. The detector of claim 15, wherein the support layer comprises a plurality of support members and a plurality of openings between support members, each support member having side surfaces facing toward an adjacent one of the openings, the side surfaces being aligned at an oblique angle relative to the first side of the support layer.

21. The detector of claim 20, wherein at least some of the support members have a cross-section that is shaped as an isosceles trapezoid.

22. The detector of claim 20, wherein the window layer comprises a continuous coating over the first side of the support members, the side surfaces of the support members and across the openings.

23. The detector of claim 15, wherein the at least one opening has a first cross-sectional area near the first side and a second, larger cross-sectional area near the second side.

24. The detector of claim 15, wherein the window layer maintains a desired pressure difference between a pressure on a first surface of the window layer near the first side and a second surface of the window layer that is closer to the second side than the first surface.

25. The detector of claim 15, wherein the window layer has a first surface aligned with the first side of the support layer.

26. A method of making an ionization window, comprising the steps of:

establishing a plurality of support members on a wafer with a plurality of spaces between the support members;

establishing a first width near one end of each the spaces;

establishing a second, larger width near a second end of each of the spaces;

coating the support members and the wafer in the spaces with a continuous ionization window layer; and removing material of the wafer adjacent the ionization window layer at the spaces between the support members to leave only the ionization window layer across the openings near the one end of the spaces.

27. The method of claim 26, comprising shaping the support members to have an isosceles trapezoid shaped cross section.

\* \* \* \* \*